United States Patent
Perry

(10) Patent No.: US 6,203,797 B1
(45) Date of Patent: Mar. 20, 2001

(54) DIETARY SUPPLEMENT AND METHOD FOR USE AS A PROBIOTIC, FOR ALLEVIATING THE SYMPTONS ASSOCIATED WITH IRRITABLE BOWEL SYNDROME

(76) Inventor: Stephen C. Perry, 205 Churchill Dr., Longwood, FL (US) 32779

( * ) Notice: Subject to any disclaimer, the term of this patent is extended or adjusted under 35 U.S.C. 154(b) by 0 days.

(21) Appl. No.: 09/479,164

(22) Filed: Jan. 7, 2000

Related U.S. Application Data

(63) Continuation-in-part of application No. 09/003,402, filed on Jan. 6, 1998, now abandoned.

(51) Int. Cl.[7] ................................................. A01N 65/00
(52) U.S. Cl. ........................................ 424/195.1; 435/101
(58) Field of Search .......................... 424/195.1; 435/101

(56) References Cited

U.S. PATENT DOCUMENTS 5,422,346  *  6/1995  Mitchell et al. ........................ 514/54
5,478,732  *  12/1995  Kunz et al. ............................ 435/101
5,968,365  *  10/1999  Laurenzo et al. ..................... 435/101
6,051,260  *  4/2000  Liska et al. ........................ 424/195.1

OTHER PUBLICATIONS

Computer Abstract Fujita GB2245143 "Aloe Leaf Products–Prepd From Vacuum Freeze Dried Aloe Leaves, Useful as Laxative, Antiinflammatory Drug Etc.", Jan. 1992.*

* cited by examiner

*Primary Examiner*—Herbert J. Lilling
(74) *Attorney, Agent, or Firm*—Malin, Haley & DiMaggio, P.A.

(57) ABSTRACT

A dietary supplement for use as a probiotic and for alleviating symptoms of irritable bowel syndrome, comprising freeze-dried aloe, fructo-oligosaccharides, and dahlia inulin juice mixture and optionally vitamin B6 (pyridoxine) manganese and L-glutamine. An additional alternate embodiments specifically for alleviation of symptoms of irritable bowel syndrome, including in the base formula bromelain and papain. Also for specific probiotic functions the following friendly bacteria: *Lactobacillus bulgaricus, lactobacillus acidophilus, lactobacillus plantarum*, and *Bifidobacterium bifidum* could be added to the base formula.

7 Claims, No Drawings

DIETARY SUPPLEMENT AND METHOD FOR USE AS A PROBIOTIC, FOR ALLEVIATING THE SYMPTONS ASSOCIATED WITH IRRITABLE BOWEL SYNDROME

CROSS-REFERENCE TO RELATED APPLICATIONS

This is a continuation-in-part of application Ser. No. 09/003,402 filed Jan. 6, 1998 by the inventors of the present invention and now abandoned.

STATEMENT REGARDING FEDERALLY SPONSORED RESEARCH OR DEVELOPMENT

Not applicable.

BACKGROUND OF THE INVENTION

1. Field of the Invention

The present invention relates to a dietary supplement and method for use as a probiotic(immuno-stimulant) and for alleviating the symptoms associated with irritable bowel syndrome.

2. Description of Related Art

The use of dietary supplements for alleviating specific symptoms associated with particular human health problems is well known. Going back to ancient times, references are made to various dietary foods, herbs, and other naturally produced substances that are associated with improving the human health condition.

Many times, a person has poor health conditions based on dietary deficiencies, such as vitamins, minerals, and other natural elements that are essential for good human health. Many times, the dietary supplements available can supply missing dietary minerals and vitamins that are essential for proper metabolism and function of the human body. Therefore, it is well known that improvements to human health and well-being can be achieved using dietary supplements, especially if they provide for deficiencies in a person's diet. The use of daily or weekly supplements supplying missing natural dietary elements such as vitamins and minerals can alleviate symptoms for improvement related to specific maladies of human health.

The human condition known as irritable bowel syndrome can best be defined as a chronic disorder of the bowels, resulting in variable abdominal discomfort or pain, constipation, diarrhea, cramps, nausea, belching, excess flatus, spasm, abdominal distention, tired and weak feeling, and mechanical irritation of the bowel. Medical treatment has traditionally entailed bland diet, mild sedatives, hydrophilic colloid laxatives, anti-cholinergics, and anti-diarrhea agents and are often associated with numerous side effects such as drowsiness, dry mouth, visual disturbances, and food intolerances.

Aloe is a tropical or subtropical plant with thick lance-shaped leaves with jagged edges and has been known for centuries for its medicinal and therapeutic properties useful in treating many different human conditions.

The aloe plant and extracts from aloe, aloe vera, and various specific aloe extracts from the natural plant can alleviate symptoms related to irritable bowel syndrome as shown in the following literature.

| Title or Subject | Authors | Date | Reference |
| --- | --- | --- | --- |
| "The Small Intestines Function Affected by Aloe Extract" | Chikalo, I. & Bolovyeve, V. Ukraine | Sept. 1966 | Quoted in "The Aloes of Tropical Africa and Madagascar" by Reynolds, G. W. |
| "Aloe Vera Gel in Peptic Ulcer Therapy; Preliminary Report" | Blitz, J., Smith, J., & Gerard, J. | 1963 | J. Amer. Osteopathic Assoc. 62 731–735 |
| Aloenin and Aloe-Ulcin From A arborescens Inhibit Gastric Secretion | Yamamoto, I. | 1970 | J. Med. Soc. Toho Jpn. 17 361 |
| Aloe-Ulcin Equals Mg Lactate | Hirata, T. & Suga, T. | 1977 | Naturforsch 32c 731 |
| Aloenin and Aloe-Ulcin From A arborescens Inhibit Gastric Secretion | Hirata, T. & Suga, T. | 1978 | Bull. Chem. Soc. Jpan. 51 842 |
| "Effect of Orally Consumed Aloe Vera Juice on Gastrointestinal Function in Normal Humans" | Bland, J. | 1985 | Preventive Medicine, March/April |
| "Effects of Aloe Extracts Aloctin A on Gastric Secretion and on Experimental Gastric Lesions in Rats" | Salto, H., Imanishi, K., Okabe, S. | 1989 | Jpn. Yakugaku Zasshi 109 (5) 335–339 |
| "A Double-Blind Trial of a Celandin, Aloe Vera and Psyllium Laxative Preparation in Adult Patients with Constipation" | Odes, H. S. & Madar, Z. | 1991 | Digestion -49 (2) 65–71 |

Freeze-dried aloe and extract from the natural aloe plant have been determined to have a positive influence as a dietary supplement and probiotic to improve the overall health and condition of a person. Specifically, freeze dried aloe and aloe extracts have been found to have antibacterial and antiviral properties.

The following information is from UK Patent No. GB 2245143B, describing a freeze-dried aloe process that could be used to prepare aloe for use in the present invention. Aloe has been extensively used as medicine. In U.S. Pat. No. 5,455,033 to Silverman, the soothing action of aloe vera extract was disclosed and utilized in an topical anti-inflammatory composition. In addition, the Silverman patent reported inulin, an ingredient in Applicant's present invention, as being an activator in the immune system and the root extract demonstrating anti-viral activity against influenza, herpes and vesicular stomatis viruses. Reference to aloe powders is also made in the Japanese Pharmacopeia. Certain low, medium, and high molecular weight compounds have been separated from aloe. For example, it is known that aloe arborescens var. natalensis (referred to hereinafter as "Kidacki aloe") contains polysaccharides such as aloetin, alcenin, aloeursin or D-mannose, aloemannan or aloe albonacite; that aloe vera contains polysaccharides; and that Cape aloe contains anthraquinonic ingredients such as aloin or aloe-emodin. Bioactive factors were separated from freeze dried aloe in U.S. Pat. No. 5,902,796 to Shand. Mixtures of these active chemical substances identified, isolated, and stabilized from aloe vera leaves have been described in U.S. Pat. Nos. 4,735,935; 4,851,224; 4,917,890; 4,957,907; 4,959, 241; and 4,966,892. One group of these active chemical substances has been referred to as aloe vera mucilaginous polysaccharides, which are comprised of oligomers and polymers of carbohydrates. The pharmaceutical application of these mucilaginous polysaccharides and uses of aloe products have been described in U.S. Pat. Nos. 5,106,616; 5,118,673; 5,308,838; 5,441,943; and 5,443,830.

Intensive attempts have been made to process aloe into medicines. Presently, as an officially allowed health food, food products prepared from Kidachi aloe have been extensively commercialized in Japan. Most of these products, however, are prepared by drying aloe leaves under the sun or by hot air and, at the time of tableting, up to about 10% of an additive such as Avicel® microcrystalline cellulose or cornstarch, is added as a binder to facilitate tableting.

It is noted that most ingredients isolated and purified from the aloe and found to be medically efficacious to animals by animal experiments, are polysaccharides, glycoproteins, or enzymes, all of which may exhibit activity in a stable condition through purification at lower temperatures. For this reason, it is generally thought to be desirable to apply as little heat as possible for the preparation of a health food or medicine from aloe.

However, since the products now available on the market are prepared by drying aloe leaves under the sun or by circulation of hot air, the polysaccharides, glycoproteins, and enzymes in them will have been thermally degraded or oxidized in the course of drying.

Furthermore, the additives for facilitating tableting, such as Avicel® or cornstarch, are added in an amount of several to tens of percents in the conventional aloe tablet products. Since a small amount of water is added under heating to knead the additives with the dried aloe mass, the resulting product undergoes further thermal degradation by such heating.

Soluble fiber in the diet is well known for its salutary effects on gastrointestinal health and for being a very good fermentation substrate for intestinal flora. Such salutary effects include providing bulk to the stool, decreasing the pH of the gastrointestinal tract, producing volatile fatty acids, decreasing intestinal transit time, and beneficially influencing various blood parameters. Dietary fiber has also been shown to have a beneficial effect on cholesterol and lipid metabolism that results in decreased serum cholesterol, triglycerides, and phospholipids and an improved (increased) HDL to LKL ratio. A study on laboratory animals showed that adding fiber to the diet decreases the incidence of bacterial translocation, i.e. corrsing the intestinal barrier and entering systemic circulation. C. Palacio et al., Dietary Fiber: Physiologic Effects and Potential Applications to Enteral Nutrition, in Clinical Nutrition: Enteral and Tube Feeding (2d. ed., 1990). Nutritional and epidemiological studies have indicated that a general increase in the consumption of dietary fiber may play a role in preventing deleterious effects of oxygen free radicals that have been involved in such processes as aging, inflammation, and some disease processes. R. Kohen et al., Prevention of Oxidative Damage in the Rat Jejunal Mucosa by Pectin, 69 Br. J. Nutrition 789 (1993).

Inulin is a naturally occurring soluble fiber, a fructo-oligo saccharide composed of a mixture of oligomers of varying degrees of polymerization or molecular weights that occurs in numerous plants, including the dahlia tuber. It is not digested in the small intestine, but is fermented in the colon. The main effects of inulin on the digestive system are a decrease in the duration of the intestinal transit, a decrease in the level of glycemia, a decrease in the lipid content in the blood, a decrease in the pH in the colon, a decrease in the constipation phenomenon and a bifidogenic effect, for example. Thus, inulin can be fermented by bifidobacteria, which has the consequence of increasing the concentration of these bacteria at the level of the intestinal flora and of decreasing the concentration of enterobacteria, in particular Clostridiae, at the level of the intestinal flora.

While prior art formulas as dietary supplements containing soluble fiber or aloe extracts are known and are generally suitable for their limited purposes, they possess certain inherent deficiencies that detract from their overall utility in restoring and maintaining gastrointestinal health. For example, a dietary supplement containing soluble dietary fiber without aloe extracts lacks antibacterial and antiviral activity. Similarly, a dietary supplement containing aloe without soluble dietary fiber lacks means for providing bulk to the stool, decreasing the pH of the gastrointestinal tract, producing volatile fatty acids, decreasing intestinal transit time, beneficially influencing various blood parameters, beneficially influencing cholesterol and lipid metabolism, decreasing the incidence of bacterial translocation, preventing deleterious effects of oxygen free radicals, and favoring the growth of beneficial bacteria in the gastrointestinal tract. Further, such prior art formulas fail to provide living intestinal bacteria that are beneficial for gastrointestinal health by providing an inhibitory effect on the growth of pathogenic bacteria, reducing the levels of toxic amines, and lowering the pH of the gastrointestinal tract.

In the prior art the production of inulin from plant materials such as Jerusalem artichoke, dahlia and chicory tubers is normally accomplished by using the following general procedure:

1. Washing the tubers;
2. Chopping, grinding or slicing the tubers;
3. Extracting the inulin from the tubers with water;
4. Treatment with Lime and Carbon Dioxide;
5. Filtering; and
6. Recovering the inulin by evaporation or precipitation.

The inulin may be subjected to heat and/or pH adjustment at some stage in the process to denature inulinase.

The biology, chemistry and analysis of inulin and related substances is reviewed in "Science and Technology of Fructans", M.Suzuki and N. J. Chatterton, Eds., CRC Press, Boca Raton, Fla. 1993. A review of technology relating to inulin is found in "Inulin and Inulin-containing Crops", S. Fuchs, Ed., Elsevier Science Publishers B. V., Amsterdam, 1993. In particular, see Vogel, "A PROCESS FOR THE PRODUCTION OF INULIN AND ITS HYDROLYSIS PRODUCTS FROM PLANT MATERIAL", pp. 65–75.

It is also known that the maintenance of a balance between the various bacteria that constitute the enterobacterial flora is closely related to man's health and, when pathogenic bacteria which are usually in the minority in the intestines become predominant, the systems of a disease develop. A typical example is diarrhea which occurs as a result of the disappearance of *Bifidobacterium bifidum* or the action of *Escherichia coli* or Staphylococcus. *Bifidobacterium bifidum* is also closely related to infant health. More specifically, *Bifidobacterium bifidum* is predominant in the enterobacterial flora of healthy infants. It is known that the feces of a dysenteric infant have a markedly lowered *Bifidobacterium bifidum* content and the relative proportions of the various bacteria in the enterobacterial flora is considerably out of balance.

On the basis of these various known facts, a typical well-balanced enterobacterial flora is now considered to be such that *Bifidobacterium bifidum*, which has excellent staying and proliferation potencies in the intestines, is most predominant at all times.

In view of the useful activities of *Bifidobacterium bifidum*, various kinds of *Bifidobacterium bifidum*-containing preparations and dairy products have recently been developed for the purpose of increasing the amount of *Bifidobacterium bifidum* in the intestines.

It is considered that the most essential factor for the proliferation of Bifidobacterium in the intestines is saccharides.

Recent, studies found that fructooligosaccharides are effective in promoting the proliferation of *Bifidobacterium bifidum*. Fructooligosaccharides (FOS) are natural substances composed primarily of fructose molecules. They belong to a group of carbohydrates that occur in many different plants. FOS are indigestible oligosaccharides that are members of the inulin subclass of fructosans, polymers composed of fructose residues. Specifically, inulins are glucofructosans, carbohydrate polymers consisting of a chain of fructose resides linked by glycosidic bonds. FOS are not hydrolyzed in the small intestine and pass through without being digested, reaching the large intestine where intact they are selectively fermented and utilized many intestinal microorganisms. FOS can be utilized efficiently by lactobacilli and bifidobacteria, species of bacteria that are beneficial for human health (Hidaka et al. "Fructooligosaccharides: Enzymatic Preparation and Biofunctions", Journal of Carbohydrate Chemistry 10(4): 509–522, 1991). Selective fermentation of FOS by Bifidobacterium leads to an increase in the presence of these bacteria and to the production of acetic acid and lactic acid as fermentation endproducts, resulting in a lower pH in the digestive tract and providing a means to prevent the overgrowth harmful bacteria like *Escherichia coli, Clostridium perfringens* and *Clostridium difficile*. (Hidaka et al., supra.) Hikada et al., also state that fermentation of FOS can also lead to an increase in the presence of short chain fatty acids and the suppression of undesirable microorganisms such as *Clostridium perfringens, C. difficile*, or *E. coli* and the toxins they produce. FOS can be utilized most efficiently by bifidobacteria, which are believed to be highly beneficial organisms (Hidaka, et al.), but cannot be utilized by certain undesirable as *E. coli* and putrefactive bacteria such as *Clostridium perfringens* or *Clostridium difficile*. It has also been shown, H. Hidaka et al., Effects of Fructooligosaccharides on Intestinal Flora and Human Health, 5 Bifidobacteria Microflora 37–50 (1986), that administration of fructooligosaccharides (FOS) enhances growth of the bifidobacteria population in the intestine, suppresses production of putrefactive factors, improves blood lipid levels in hyperlipidemia patients and provides relief from constipation.

Fructooligosaccharides (FOS) can be produced enzymatically through chemical techniques or by extraction from natural substances. FOS occur in nature in many kinds of plants, including onions, dahlias, garlic, shallots, artichokes, wheat, rye, bananas, asparagus and tomatoes, that are commonly part of a human diet (Speights et al., "Fructooligosaccharides-A Low Caloric Bulking Agent And More From Sucrose", Carbohydrates in Industrial Synthesis, ed. M. A. Clarke, Proceedings of the Symposium of the Division of Carbohydrate Chemistry of the American Chemical Society, 1992).

It has been shown, A. Hata, The Influence of Neosugar on the Lipid Metabolism of Experimental Animals, Proc. 1$^{st}$ Neosugar Res. Conference, Tokyo (1982), that fructooligosaccharides (FOS) in the diet of experimental animals cause reduction of blood sugar, serum cholesterol, triglycerides, phospholipids; significant improvement in the HDL/LDL ratio; an increase in free fatty acids; and significant decreases in total cholesterol in lipidemia cases.

Animal toxicology studies have shown no evidence of toxicity, mutagenicity, or carginogenic effects due to FOS (Clevenger et al., "Toxicological evaluation of neosugar: genotoxicity, carcinogenicity, and chronic toxicity", Journal of the American College of Toxicology 7:643–622, 1988). Indigestible oligosaccharides such as FOS can be added to a nutritional product to create an environment in the gastrointestinal tract that is not conducive to the growth of microbial pathogens. Such a nutritional product can also be useful in the prevention of diarrhea caused by these pathogens. FOS is used in Japan in many food products and has been added to infant formula (Fructooligosaccharide Information Package, Coors Bio Tech, Inc. May 1990).

Certain bacteria have also been shown to be beneficial to human gastrointestinal health. The intestinal flora of the human gut contains some $100.\text{times}.10.\text{sup}.9$ viable bacteria, representing 100 or more different species. The major bacteria of the intestine can be roughly divided into three groups: (a) lactic acid bacteria, including lactobacilli, bifidobacteria, and streptococci; (b) anaerobic bacteria; and (c) aerobic bacteria.

Bacteria of the genus Lactobacillus have been used for several hundred years for treating various illnesses. Lactobacilli found in the human intestinal tract include *L. acidophilus, L. casei, L. fermentum, L. salivaroes, L. brevis, L. leichmannii, L. plantarum,* and *L. cellobiosus*. In recent years, *L. acidophilus* has been shown to be exceptionally useful in treating conditions such as antibiotic-induced imbalances in the gastrointestinal microflora, hypercholesterolemia, vaginal infections, *E.coli* infection, oral contraceptive failure, depressed immunity, cancerous tumors, chronic granulomatous disease, and lactose indigestion. A. G. Shauss, Method of Action, Clinical Application, and Toxicity Data, 3 J. Advancement Med. 163 (1990). In vitro studies have shown *L. acidophilus* to have an inhibitory effect on the growth of pathogenic bacteria such as Campylobacterpylori, *Staphylococcus aureus, Pseudomonas aeruginosa,* and *Sarcina lutea*. K. M. Shahani et al., Natural Antibiotic Activity of Lactobacillus Acidophilus and Bulgaricus, 11 Cultured Dairy Products J. 14 (1976).

The beneficial effect of *L. acidophilus* is further illustrated by preliminary evidence that *L. acidophilus* inhibits the toxic activities of bacteria in patients with chronic kidney failure. M. L. Simenhoff et al., Biomodulation of Uremic Pathophysiology in Man, abstract presented at Am. Soc. Of Nephrology Meeting, Baltimore, 1992. Such patients often have toxic levels of amines in their blood due to bacterial overgrowth in the small bowel. Consumption of high levels of freeze dried bacteria drastically reduces levels of these toxic amines. These results demonstrate the ability of *L. acidophilus* to exert a positive effect on the microflora of the intestines.

Bifidobacteria are also known to exert a beneficial influence on human health. These bacteria exert antimicrobial activity in the human intestine by producing lactic acid and acetic acid as a result of carbohydrate metabolism. These acids lower the intestinal pH, thereby inhibiting overgrowth of gastrointestinal pathogens. Therapeutic applications of bifidobacteria are indicated for the management of diarrhea and constipation, and the management of hepatic encephalopathy with hyperammonemia. Additional benefits include the production of B vitamins and breakdown of carginogenic N-nitrosamines.

Bifidobacteria can be significantly reduced in elderly ispeople due to a reduction of secreted gastric juices. The bifidobacteria population in adults is much more stable, however, changes in the diet, administration of antibiotics, exposure to gamma radiation or x-rays, disease, stress and other disturbances can result in overgrowth of potentially pathogenic bacteria, decrease in beneficial bacteria (lactobacilli and bifidobacteria), and in the gut is associated with various forms of diarrhea, susceptibility to systemic infections, constipation, vague and acute abdominal symptoms, fatigue, dyspepsia, and presence of carcinogenic metabolites. Reestablishment of a normal balance of gastrointestinal flora can be accelerated, and such normal balance maintained, with dietary administration of lactobacilli and/or bifidobacteria such as in the present invention. Even when the Bifidobacteria have become temporarily predominant in intestines, its influence may readily change. Thus, it is preferred to promote the growth of not only Bifidobacteria but also other useful bacteria such as lactic acid bacteria in order to stably obtain the effect of improving intestinal floras. In other words, the influence of lactic acid bacteria and so forth may also be increased together with that of Bifidobacteria.

Lactobacilli and bifidobacteria produce organic acids that reduce intestinal pH and thereby inhibit the growth of acid-sensitive undesirable bacteria. Lactobacilli produce lactic acid, hyrdrogen peroxide, and possibly acetic and benzoic acids. Bifidobacteria produce short chain fatty acids (SCFA) such as acetic, propionic, and butyric acids, as well as lactic and formic acids. The most plentiful short chain fatty acid produced by bifidobacteria is acetic acid, which has a wide range of antimicrobial activities against yeasts, molds and other bacteria. Additionally, short chain fatty acids support normal gastrointestinal function by increasing colonic blood flow, stimulating pancreatic enzyme secretion, promoting sodium and water absorption, and potentiating intestinal mucosal growth. Bifidobacteria are also known to deconjugate bile salts to free bile acids, which are more inhibitory to susceptible bacteria than are the conjugated forms. Further, lactobacilli and bifidobacteria are able to produce other antimicrobial substances, such as bacteriocins, that inhibit the growth and proliferation of harmful bacteria in the gut.

In view of the foregoing, it will be appreciated that a composition for alleviating irritable bowel symptoms and for improving and maintaining gastrointestinal health comprising aloe, that has antibacterial and antiviral activity, and soluble dietary fibers such as fructo-oligosaccharides and inulin, that provide the typical advantages of dietary fiber and additionally are low in calories, does not affect blood glucose or insulin levels, further including beneficial/friendly bacteria which favor the growth of other beneficial bacteria in the gastrointestinal tract while at the same time inhibiting the growth of potentially pathogenic or harmful microorganisms would be a significant advancement in the art.

BRIEF SUMMARY OF THE INVENTION

The present invention is a dietary supplement for alleviating symptoms of irritable bowel syndrome and for use as a probiotic, comprising highly concentrated freeze-dried aloe, especially prepared as described below, fructo-oligosaccharides, and dahlia inulin juice mixture and optionally vitamin B6 (pyridoxine HCI), manganese and L-glutamine.

As another alternative embodiment of the invention, the composition, as a dietary supplement could include the basic formula discussed above, along with friendly bacteria which are aimed at the probiotic function specifically, such as *Lactobacillus bulgaricus; Lactobacillus acidophilus; Lactobacillus plantarum*; and *Bifidobacterium bifidum*. These bacteria have been selected as having been proven to be beneficial to normal digestive functions by keeping healthy flora thriving in the intestinal tract and keeping out potential pathogens.

For an improved combined dietary supplement in accordance with yet another alternate embodiment of the invention, we could take the basic formula described above based on the freeze-dried aloe, add bromelain and papain along with the friendly bacteria for the probiotic function to have a dietary supplement composition that can accomplish both functions simultaneously. Applicant believes that the ingredients selected work synergistically to achieve improved results, both for the irritable bowel syndrome and as a probiotic.

It is object of this invention to provide a method and composition of natural ingredients as a dietary supplement that can function both as a probiotic and, at the same time, be used to alleviate symptoms of irritable bowel syndrome while improving intestinal flora.

In accordance with these and other objects which will become apparent hereinafter, the instant invention will now be described with particular reference to the accompanying drawings.

DETAILED DESCRIPTION OF THE INVENTION

A dietary supplement for use as a probiotic for human beings and for alleviating symptoms commonly found with irritable bowel syndrome in human beings, comprising freeze-dried aloe, (preferably from the Aloe Vera Linne plant), fructo-oligosaccharides, and dahlia inulin juice mixture. Optionally, and in the preferred embodiment, pyridoxine hydrochloride (vitamin B6), manganese, L-Glutamine may be added.

The above ingredients in the proper formulation have been found effective for both probiotic functions for human beings and also to alleviate symptoms of irritable bowel syndrome. The aloe must be freeze-dried in accordance with the above-described process for aloe leaves. Further, the freeze-dried aloe is prepared in such a way that all the water is removed, so that the final extract is approximately 200 to 1 pure aloe leaf extract.

In an alternate embodiment, for an improvement specifically designated as a composition for alleviating symptoms of irritable bowel syndrome, in addition to the above ingredients, bromelain and papain are added in specific amounts to act as an antiinflammatory and are especially useful for the bowels.

The present invention begins with the proper preparation of freeze-dried aloe. In particular, Applicant believes that if properly prepared, the freeze-dried aloe extract can have a more beneficial result as a dietary supplement if it is in a high strength, which Applicant achieves 200 to 1 pure freeze-dried aloe, and if the extract is not heated above room temperature in its preparation.

It has been found that the freeze-dried aloe (Aloe Vera Linne), which is in concentrations of 200 to 1, should be from 25 to 200 parts of the composition. The pyridoxine hydrochloride (vitamin B6) should be from 10 to 100 parts. The manganese used herein would be in 30 to 150 parts of the composition. L-Glutamine should be 150 to 300 parts. The fructo-oligosaccharides should be from 100 to 200 parts, and the dahlia inulin juice mixture should be from 25 to 200 parts. These parts are related to the weight of the product. As an example, the product should be given daily, from 800 mg to 1500 mg, in a capsule or tablet form.

EXAMPLE 1

|  | w/w |
| --- | --- |
| Freeze-dried aloe (Aloe Vera Linne Plant) | 200/1 strength 100 parts |
| Vitamin B6 | 55 parts |
| Manganese | 90 parts |
| L-Glutamine | 225 parts |
| Fructo-oligosaccharides | 150 parts |
| Dahlia inulin juice mixture | 112.5 parts |

To provide a specific dietary supplement that also further enhances the alleviation of symptoms associated with irritable bowel syndrome, we would add to the above general formula bromelain (35 to 160 parts) and papain (50 to 170 parts).

EXAMPLE 2

In addition to that shown in Example 1, we would add the following:

| Bromelain | 97.5 parts |
| --- | --- |
| Papain | 110 parts |

In order to enhance the probiotic function of the basic formula shown in Example 1, we can also add friendly bacteria which would include *Lactobacillus bulgaricus* (250,000,000 to 1,000,000,000 CFU); *Lactobacillus acidophilus* (250,000,000 to 1,000,000,000 CFU); *Lactobacillus plantarum* (250,000,000 to 1,000,000,000 CFU); and *bifidobacterium bifidum* (250,000,000 to 1,000,000,000 CFU).

EXAMPLE 3

| *Lactobacillus bulgaricus* | 500,000,000 CFU |
| --- | --- |
| *Lactobacillus acidophilus* | 500,000,000 CFU |
| *Lactobacillus plantarum* | 500,000,000 CFU |
| *Bifidobacterium bifidum* | 500,000,000 CFU |

The aloe process provides:
1. A vacuum freeze-dried mass of homogenized entire leaves of a plant belonging to the genus Aloe (preferably *Aloe Vera Linne* also known as *Aloe Barbadensis*).
2. A method for producing a vacuum freeze-dried mass of the leaves of a plant belonging to the genus Aloe or (preferably *Aloe Vera Linne* also known as *Aloe Barbadensis*), the method comprising homogenizing entire leaves of the plant and then vacuum freeze-drying the homogenate.
3. A tablet formed from a vacuum freeze-dried mass of homogenized entire leaves of a plant belonging to the genus Aloe or preferably *Aloe Vera Linne* also known as *Aloe Barbadensis*.
4. A method for producing a tablet of a vacuum freeze-dried mass of the leaves of a plant belonging to the genus Aloe or preferably *Aloe Vera Linne* also known as *Aloe Barbadensis*, the method comprising:

(a) homogenizing entire leaves of the plant;
(b) vacuum freeze-drying the homogenate;
(c) granulating the vacuum freeze-dried mass; and
(d) compacting the resulting granules into tablets.

The vacuum freeze-dried mass is suitably in the form of granules. The homogenization may be carried out under cooling. The tablet of the invention may consist solely of the vacuum freeze-dried mass or may include a further nutrient and/or medicinal ingredient, which may have been incorporated in any of steps (b) to (d) of the production method of the tablet.

The dried mass, granule, or the tablet according to the invention exhibits the following properties:

1. it presents a pale color;
2. it has a grassy smell;
3. it has a strongly bitter taste;
4. it is soluble in water, while being partially insoluble in methanol, ethanol, or acetone;
5. in protein determination reactions, it is positive both in bicinchoninic acid (BCA) reaction and in Lowry-Folin reaction;
6. as to saccharide determination reactions, it is positive in the anthrone sulfuric acid reaction and in the phenol sulfuric acid reaction;
7. as to proteolytic enzyme activities, it has activities of carboxypeptidase and trypsin, and it has also protease-inhibitory activity;
8. it exhibits positive cell agglutination activity with erythrocytes and weakly positive cell agglutination activity with cancer cells; and
9. it exhibits weakly positive blastogenetic activity with lymphocytes.

Each of the dried mass, the granule and the tablet of the plant belonging to the genus Aloe or (preferably *Aloe Vera Linne* also known as *Aloe Barbadensis*) according to the invention contains the medicinal ingredients endogenously contained in that plant, such as polysaccharides, glycoproteins, and enzymes, in a state substantially free from degradation caused by heating or oxidation. A variety of physiologically active substances, found by animal experiments to be contained in the plant such as aloin or aloe carboxypeptidase, are also present without undergoing thermal degradation. Hence, the dried mass, granule, or tablet according to the invention may be beneficial for its laxative, gastrointestinal and anti-ulcer, anti-inflammatory, anti-fungal, anti-hyperglycemia, anti-burn edema effects, and as an immunomodulator.

The tablet of the aloe process may consist of 100% of the above-mentioned dried mass, no additive for tableting being necessary, so that a high-quality tablet is provided which contains the medicinal ingredients of the plant belonging to the genus Aloe (preferably *Aloe Vera Linne*) with a high purity.

The tablet of the aloe process is easy to swallow, however, has a strong, bitter taste and flavor displayed when chewed.

In the method for producing the dried mass of the aloe, the liquid obtained by crushing the leaves of the plant belonging to the genus Aloe (preferably *Aloe Vera Linne*) is freeze-dried in vacuum, without resorting to the step of drying the liquid by heating at a temperature higher than the ambient temperature. Therefore, the dried mass containing the above-mentioned medicinal ingredients in the plant is prepared without degrading those ingredients.

According to the method for preparing the granules of the aloe, the dried mass is press-molded into granules, and the granules contain the medicinal ingredients without thermal degradation.

In the method for producing the tablet of the aloe, the dried mass is press-molded into granules, and then tableted. Thus, the tablet contains the medicinal ingredients without thermal degradation. Since no additive for facilitating tableting is required, tablets containing the medicinal ingredients in higher percentages are produced. Thus, the tablet may contain up to 100% of effective ingredients in the dried mass.

The aloe, based on numerous historical references, some of which are cited herein, provides proven alleviation of symptoms on the digestive tract of humans. The freeze-dried aloe composition is made up of various chains of mucopolysaccharides (MPS) the physiological activities of which have been described in U.S. Pat. Nos. 5,10,515; 5,118,674; 5,308,838; 5,441,943 and 5,443,830 and include anti-viral, anti-tumor, immune-stimulants, immune-modulators, vaccine adjuvants, means of reducing opportunistic infections and controlling inflammations, means of stimulating the healing process, and treatment for gastric ulcers.

It is believed that vitamin B6 is an important co-enzyme in breaking down the utilization of proteins, fats, and carbohydrates. It also plays an important role as a precursor of enzymes responsible for forming MPS and inhibiting the breakdown of MPS. Manganese is a necessary element in the utilization of sulfate for the MPS synthesis, and it also inhibits degradation of MPS. L-Glutamine aids in mineral absorption, protects against peptic ulcers, as well as protecting digestive tract bacteria from alcohol poisoning. It also acts as a nutrient co-factor with vitamin B6. Fructo-oligosaccharides are well-known in the art as short chain polymers of simple carbohydrates (fructose and sucrose) which pass through the body unabsorbed and act as a metabolic enhancer for intestinal microorganisms and bacteria, especially bifidal bacteria. In one of many articles published based on research by the Japanese, e.g. "Effects of Fructooligosaccharides on Intestinal Flora and Human Health", Bifdobacteria Microflora, Vol. 5(1) p. 37–50, 1986, it was reported that fructo-oligosaccharides which have been synthesized from sucrose are well utilized by bifidus bacteria and have been used to promote bifidus cultures in the gut as well as improved blood lipids in hyperlipidemia and suppressed the production of intestinal putrefactive substances. In an alternate embodiment of the invention, the basic composition disclosed herein may include additions of positive enhancing bacteria that are used with fructooligosaccharides. The bifidal bacteria exhibit inhibitory effects on many pathogenic organisms, such as salmonella, *candida albicans* and staphylococcus.

The advantages of soluble dietary fiber have been briefly reviewed above. Inulin is one such fiber. Inulin is a storage carbohydrate found in many plants including onion, asparagus, artichoke and dahlia tubers. It is the optimum food for probiotic bacteria, consisting of many fructose monosaccharides. Inulin has been an important food in Europe for many years and is currently being used as a source of dietary fiber, for replacing fat in the diet, and for promotion growth of beneficial bacteria in the intestine. In the U.S., inulin is added to all types of noodles. It has moderately sweet taste, is high soluble, and is a frequent replacement for sugar in many foods. Medically, inulin is the substance of choice to study renal clearance and impaired kidney function. Inulin is a large molecule and probably a mixture of various sized fructose polymers. Inulin exists in a soluble state in the tuber. By immediately pressing the comminuted tuber, the majority of the inulin can be removed from the plant resulting in a juice rich in inulin, i.e. dahlia inulin juice. Subsequent cooling of the pressed inulin juice results in the precipitation of the desired "crude" inulin. U.S. Pat. No. 5,422,346 assigned to California Natural Products which is incorporated herein by reference, fully discusses inulin, its clinical use, physical and chemical properties, preparation, derivation, purification and commercial development. The 346' patent discloses a process for producing an inulin juice polymer mixture for metabolic purposes. U.S. Pat. No. 4,283,432 to Mitchell discloses a process and the dahlia flavor powders produced by grinding, separating, concentrating, and roasting of the water solubles of the dahlia tuber. In U.S. Pat. No. 4,285,735 also to Mitchell, a process is disclosed for making a fructose polymer mixture containing chiefly inulin, inulides, protein, color, flavor, and minerals by a non-heat, non-water separation of the water solubles from the ground tuber and subsequently crystallizing the clear concentrated extract. The inulin produced from the 735' process is the preferred material used in the present invention for the raw inulin product.

The invention is described herein particularly with reference to the dahlia tuber, however, it is thought that the principles thereof are applicable to any inulin containing naturally-occuring material. In the composition according to the present invention, inulin, is included in addition to fructo-oligosaccharides.

Fructo-oligosaccharides (FOS) are another type of soluble dietary fiber. FOPS is widely distributed in nature and is found in honey, bear, onion, asparagus, Chinese chive, banana, maple sugar, oats Jerusalem artichoke and the dahlia plant.

The physiological activity possessed by fructo-oligosaccharides has recently become of major interest ["KagaKue to Seibutsu" (Chemistry and Biology), Vol. 21, p. 291). For example, fructo-oligosaccharides are difficult to digest and are selectively utilized by useful intestinal flora, *Lactobacillus bifidus* in particular, thereby promoting proliferation of these organisms and improving Taxation and the like. In addition, when broken down by *Lactobacillus bifidus*, organic acids are produced, which are thought to reduce cholesterol levels in the body.

Upon ingestion, both inulin and FOS are hydrolyzed to a negligible extent as they pass through the mouth, stomach, and small intestine. In the large intestine, they are readily fermented by the intestinal mircoflora. These carbohydrates are metabolized by the bacteria into short chain fatty acids, mainly acetic, propionic, butyric, and lactic acids. As a consequence of this fermentation, a considerable amount of bacterial mass is produced, which increases stool wet weight. The short chain fatty acids are absorbed by the large intestine and are further metabolized in the liver. This allows the body to recover some energy from inulin and FOS, although the efficiency of energy conversion is markedly lower than with other carbohydrates. This phenomenon underlies the low calorie content of fructans and dietary fibers.

Inulin and FOS are used as a source of energy in the intestinal tract mainly by bacteria in the genus Bifidobacterium. H. Hidaka et al., Effects of Fructooligosaccharides on Intestinal Flora and Human Health, 5 Bifidobacteria Microflora 37–50 (1986). When inulin and FOS are administered in the diet, the bifidobacteria increase significantly, becoming the predominant bacteria in the intestinal population, and the clostridia, which are a measure of potentially pathogenic microorganisms, are significantly reduced. Other important groups of bacteria in the mixed population in the intestines, such as Fusobacterioum, Lactobacillus, and aerobic bacteria, are not significantly affected by the administration of inulin and FOS. H. Hidaka et al., Effects of Fructo-oligosaccharides on Intestinal Flora and Human Health, 5 Bifidobacteria Microflora 37–50 (1986).

The following positive effects are obtained by addition of inulin and fructo-oligosaccharides(FOS) to a composition for use as a dietary supplement according to the present invention: reduction of intestinal disorders, enhancement of a balanced intestinal microflora, and remediation of constipation.

The present composition of dietary supplement described above can also, in an alternate embodiment, specifically address irritable bowel syndrome by adding bromelain and papain. Bromelain is an enzyme found only in pineapples and it aids in the digestion of heavy fats and also acts as an anti-inflammatory. Studies have shown that it increases permeability of the digestive tract, providing better absorption of nutrients. Papain is an enzyme from unripe papaya which aids in the digestion of proteins, and has been proven to loosen necrotic and encrusted waste material from the intestinal walls.

As another alternative embodiment of the invention, the composition as a dietary supplement could include the basic formula discussed above, along with friendly bacteria which are aimed at the probiotic function specifically, such as *Lactobacillus bulgaricus; Lactobacillus acidophilus; Lactobacillus plantarum*; and *Bifidobacterium bifidum.*

Bacteria have been selected as having been proven to be beneficial to normal digestive functions and a healthy digestive tract. These bacteria are instrumental in keeping healthy flora thriving in the intestinal tract and keeping out potential pathogens. It is really preferable that the formulation contain at least one type of beneficial human intestinal microorganism for restoring and maintaining good gastrointestinal health. The beneficial human intestinal microorganism is preferably a member selected from the group consisting of lactobacilli and bifidobacteria. Preferred lactobacilli include *L. acidophilus, L. bulgaricus, L plantarum*, or combination thereof. Preferred bifidobacteria is *B-bifidum*. Such beneficial human intestinal bacteria can be added to the base formulation in an amount 500,000,000 CFU each by weight.

Applicant believes that the determined efficacy of the composition of the above examples reveals there is a synergistic effect from the combination of elements of the composition within the established range of proportions provided.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A dietary supplement for use as a probiotic and for alleviating the symptoms associated with irritable bowel syndrome, comprising the following ingredients by weight:
   freeze-dried *Aloe Vera Linne* plant, 25–200 parts;
   vitamin B6 (pyridoxine hydrochloride), 10–100 parts;
   manganese, 30–150 parts;
   L-Glutamine, 150–300 parts;
   fructo-oligosaccharides, 100–200 parts, and in addition thereto,
   dahlia inulin juice mixture, 25–200 parts.

2. A dietary supplement as in claim 1, specifically for alleviating the symptoms of irritable bowel syndrome, further comprising the following ingredients by weight:
   bromelain, 35–160 parts; and
   papain, 50–170 parts.

3. A dietary supplement as in claim 2, for use as a probiotic and to alleviate the symptoms of irritable bowel syndrome, further comprising:
   *Lactobacillus bulgaricus*, 500,000,000 CFU;
   *Lactobacillus acidophilus*, 500,000,000 CFU;
   *Lactobacillus plantarum*, 500,000,000 CFU; and
   *Bifidobacterium bifidum*, 500,000,000 CFU.

4. A dietary supplement for use as a probiotic as in claim 2, wherein said freeze-dried *Aloe Vera Linne* is made by the process of homogenizing entire leaves of the plant, vacuum freeze-drying the homogenate, granulating the vacuum freeze-dried mass and compacting the resulting granules into tablets.

5. The method of alleviating the symptoms of irritable bowel syndrome and for use as a probiotic in the body of a mammal to be treated comprising the step of daily oral administration to said mammal of the dietary supplement mixture comprising by weight (a) 25–220 parts freeze dried *Aloe Vera Linne* Plant; (b) 100–200 parts fructo-oligosaccharides; (c) 25–200 parts dahlia inulin juice mixture in addition to (b); (d) 10–100 parts vitamin B6; (e) 30–150 parts manganese; and (f) 150–300 parts L-Glutamine in amounts effective to alleviate the symptoms of irritable bowel syndrome and for use as a probiotic.

6. The method of claim 5 further comprising by weight:
   bromelain 35–150 parts; and
   papain, 50–170 parts.

7. The method of claim 6 wherein said dietary composition further comprises by weight at least 500,000,000 CFU of one type of beneficial human intestinal microorganism selected from the group consisting of *Lactobacillus bulgaricus, L. acidophilus, L. plantarum*, and *Bifidobacterium bididum* or a combination thereof.

* * * * *